US00PP12482P2

(12) United States Plant Patent
Pansing et al.

(10) Patent No.: US PP12,482 P2
(45) Date of Patent: Mar. 26, 2002

(54) CRABAPPLE TREE NAMED 'MALUSQUEST'

(76) Inventors: Jeffrey M Pansing; Karen R. Pansing, both of 2100 N. Preble County Line Rd., West Alexandria, OH (US) 45381

( * ) Notice: Subject to any disclaimer, the term of this patent is extended or adjusted under 35 U.S.C. 154(b) by 0 days.

(21) Appl. No.: 09/515,418

(22) Filed: Feb. 29, 2000

(51) Int. Cl.[7] ..... A01H 5/00
(52) U.S. Cl. ..... Plt./173
(58) Field of Search ..... Plt./173

(56) References Cited

U.S. PATENT DOCUMENTS

PP3,267 P 12/1972 Collins
PP6,672 P 3/1989 Fiala
PP8,478 P 11/1993 Fiala et al.
PP8,658 P 3/1994 Tustin
PP9,881 P 5/1997 Janick et al.

*Primary Examiner*—Bruce R. Campell
*Assistant Examiner*—Annette Para
(74) *Attorney, Agent, or Firm*—Jacox, Meckstroth & Jenkins

(57) ABSTRACT

A new and distinct cultivar of crabapple (*Malus×domestica*) was created during the course of a plant breeding and selection program for the development of improved crabapple cultivars with persistent winter fruit and good disease resistance. Attractive glossy bright to dark red ornamental fruits are formed that commonly persist with minimal shrinkage into February of the following year. The overall growth habit is compact and upright and yields a tree having a pleasing pyramidal-spreading configuration. Good Good winter hardiness is provided combined with resistance to apple scab, apple mildew, fireblight and cedar-apple rust.

5 Drawing Sheets

SUMMARY OF THE INVENTION

A new and distinct cultivar 'Malusquest' is a flowering crabapple tree (*Malus×domestica*) which originated as a seedling from a cross of Malus 'Jewelcole' (non-patented in the United States) as the seed parent with Malus×'Prairiefire' (non-patented in the United States) as the pollen parent. Malus 'Jewelcole' was selected by William D. Collins of Circleville, Ohio. Malus 'Prairiefire' was developed by Dr. Daniel F. Dayton, Department of Horticulture, University of Illinois, Urbana. This cross was made on May 1, 1984 in a field of crabapple trees located at 2100 N. Preble County Line Road, West Alexandria, Ohio. The new cultivar of the present invention initially was designated 'RJ-PR-87'.

The new and distinct cultivar of *Malus×domestica* plant possesses the following combination of characteristics:

(A) Flowers borne in clusters from deep red buds that open to a soft pink flower during the extended blooming period;
(B) Attractive dark green glossy foliage and smooth attractive cherry-like bark with a slight sheen,
(C) Abundant production of clusters of very firm, small, glossy, bright to dark red fruits that persist and remain glossy and ornamental into February of the following year, with minimal shrinking or shriveling;
(D) Exhibits resistance to destructive diseases of Malus, including apple scab, apple mildew, fireblight, and cedar-apple rust;
(E) Forms a desirable compact, upright, pyramidal-spreading tree habit, having a sturdy trunk bearing well-spaced, well-arranged branches that diverge from the trunk at wide angles;
(F) Exhibits good winter hardiness, being undamaged and productive after winters reaching at least to a very cold 30 degrees below zero Celsius; and
(G) Disease resistance and heavy productivity of attractive flowers and fruits as well as attractive plant habit, exhibits exceptional merit for planting as a landscape ornamental and for wildlife.

The new cultivar is named 'Malusquest' and consistently bears an abundance of small glossy bright to dark reddish-maroon fruits which persist through late winter. Comparison against susceptible flowering crabapple varieties planted in close proximity demonstrated that the new cultivar exhibits: 1) good resistance to apple scab disease caused by *Venturia inequalis* (Cke.) Wint.; 2) moderate resistance to fire blight disease caused by *Erwinia amylovora* (Burr.) Winslow; 3) good resistance to powdery mildew caused by *Podosphaera leucotricha* (Ell. and Ev.) Salm.; and 4) resistance to cedar-apple rust caused by *Gymnosporangium juniperi-virginianea* (Schw).

Flowering begins in early-season, five days earlier than either of the parent cultivars, usually late April in Dayton, Ohio, depending on the variations in degree days each season. Flowering occurs in clusters of up to seven single pink flowers borne both on spurs and in leaf axils on the current-year's growth. The axillary flowers develop later than those on the spurs, extending the flowering period up to a week longer. During peak bloom, the masses of flowers are exceptionally fragrant. The fragrance is a pleasing sweet aromatic perfume.

After selection, the new cultivar was asexually propagated by budding on MIII and *domestica* rootstocks. Such asexual propagation was first carved out at 11140 Milton-Carlisle Road, New Carlisle, Ohio during August, 1995. On the budded trees, the scions have retained the definitive characteristics after propagation. Two year budded plants often set flowers and fruit while less than 90 cm. in height. The typical upward to slightly horizontal branching habit is evident at an early age.

The new cultivar of the present invention can be readily distinguished from each of its parents and all other previously-known cultivars in view of the combination of characteristics described herein. For instance, the flowers of the 'Jewelcole' cultivar are pure white unlike the bright rose changing to lighter pink of the new cultivar, and the flowers of the 'Prairiefire' cultivar are bright crimson red. The fruit of the 'Prairiefire' cultivar tends to be soft and to drop shortly after the first frost and is not well retained on the tree as is the firm fruit of the new cultivar. Also, the foliage of the 'Prairiefire' cultivar is of a dissimilar red-maroon coloration that ages to reddish-green unlike the deep green foliage coloration of the new cultivar.

BRIEF DESCRIPTION OF THE FIGURES

Trees of the new variety have been grown at 11140 Milton-Carlisle Road, New Carlisle, Ohio exclusively for the owner. Starting in August 1995, they were budded on domestics rootstocks. Since 1996, budding has been done on MIII rootstocks. Trees are then grown for fifteen months to the "Liner" stage. They are drug and transplanted at 2100 North Preble County Line Road, West Alexandria, Ohio.

DETAILED DESCRIPTION OF THE NEW CULTIVAR

Figure 1:
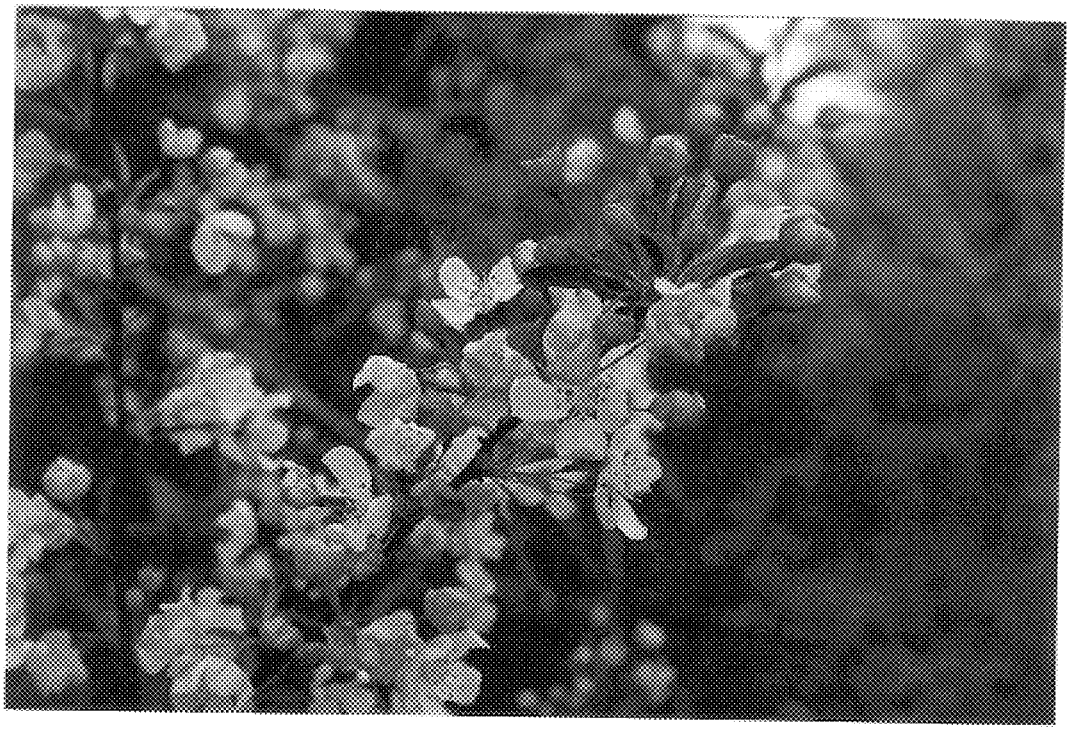
FIG. 1 shows flower buds and early anthesis of 'Malusquest' (Seedling #RJ-PR-87); approximate date observed was Apr. 25, 1999.
Figure 2:
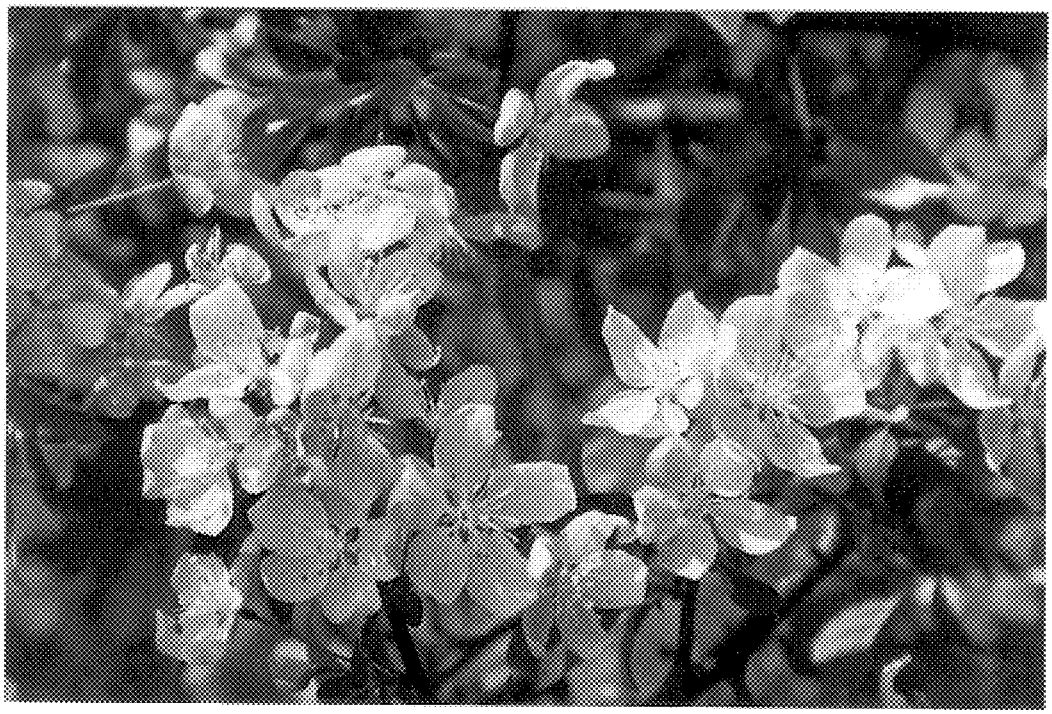
FIG. 2 shows mature flowers of 'Malusquest'; approximate date observed was May 9, 1999.
Figure 3:
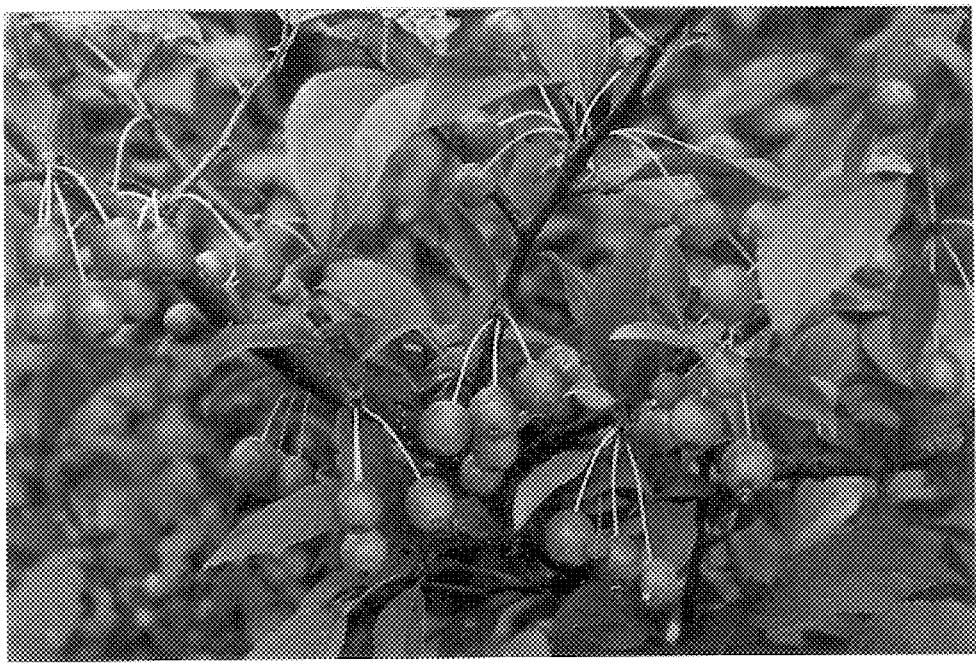
FIG. 3 shows mature foliage of 'Malusquest'; approximate date observed was Aug. 14, 1999.
Figure 4:
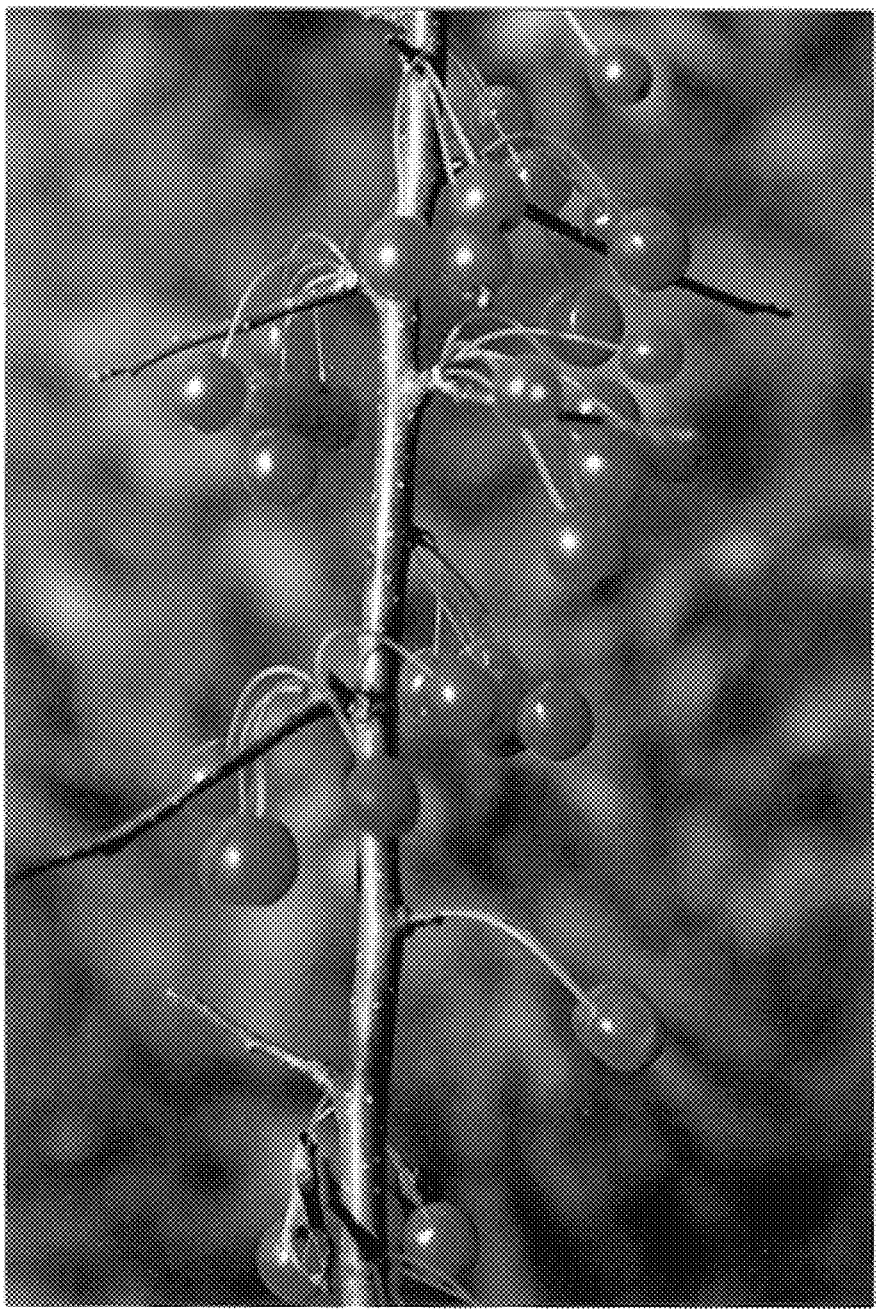
FIG. 4 shows mature fruit of 'Malusquest'; approximate date observed was Oct. 15, 1999; and, FIG. 5 shows mature lenticels on a five-year old trunk of 'Malusquest'; approximate date observed was Jan. 15, 1999.
Figure 5:
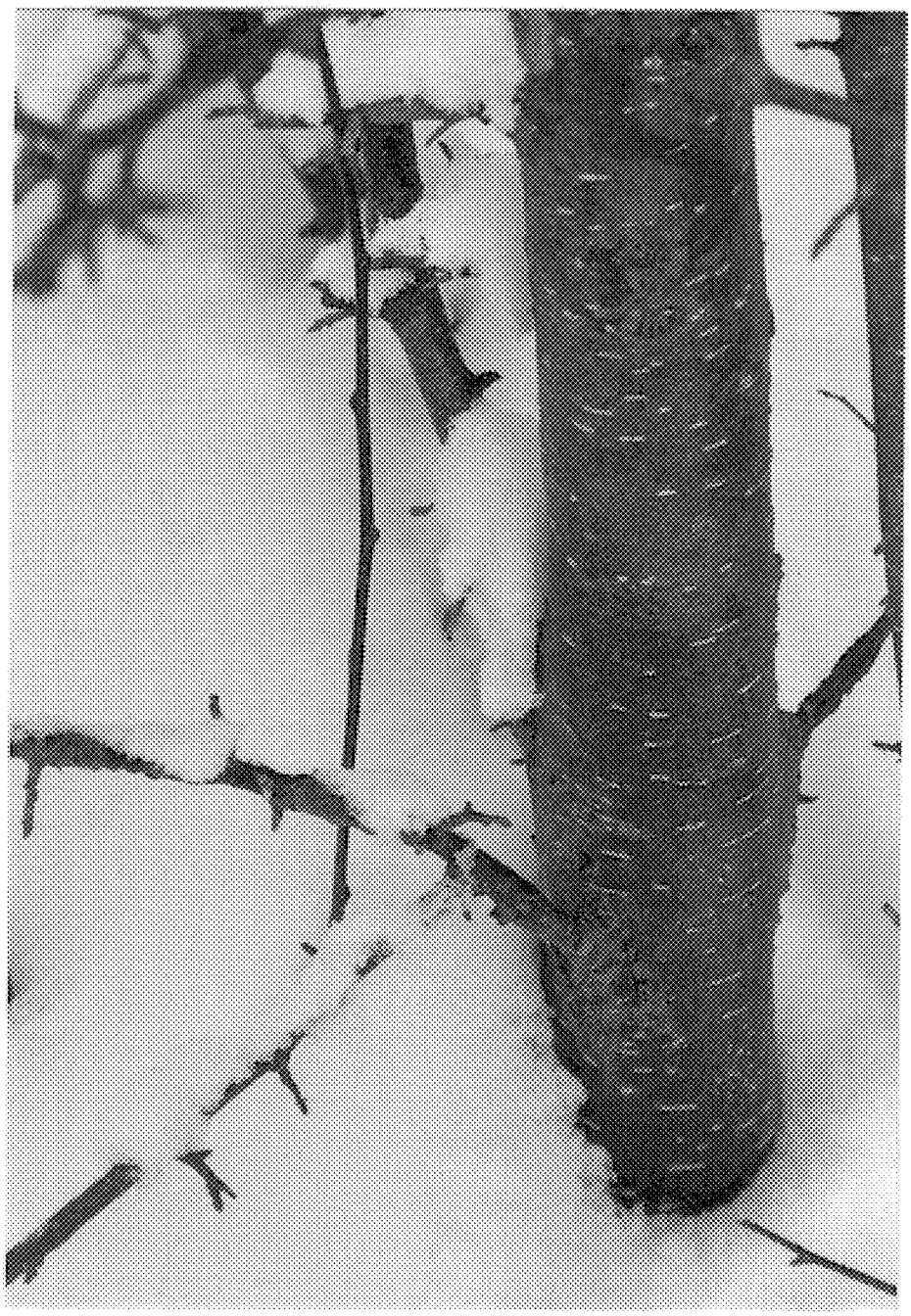

FIGS. 1, 2, 3, 4, and 5 are color photographs which illustrate typical examples of the flower bud clusters, flowers, leaves, fruit, and trunk, respectively, of 'Malusquest'. Photographs were taken at 2100 North Preble County Line Road, West Alexandria, Ohio. The observed plants are four years old and have been "budded" on MIII rootstocks. In the following detailed descriptions, the color name designations followed by numbers were determined by comparison with the Horticultural Colour Chart (2 Vols.) Wilson, R. F., published by The Royal Horticultural Society, London.

FLOWERS

Flowers are annually borne abundantly, commonly five (up to seven) per cluster, with the clusters well distributed on the branches. The flowers are prominently displayed on long, stiff pedicels, approximately 30–40 mm. in length. The color of the open flowers is essentially a pink blush to a very faint soft pink blush. The flowers are single, having five petals each with a short claw. The form of individual flowers is sometimes irregular. Typical flowering time is the last week of April through mid-May at 2100 North Preble County Line Road, West Alexandria, Ohio.

Corolla: Average diameter of approximately 40 mm at anthesis, composed of five separate petals.

Petals: Concave, average size approximately 18 mm long× approximately 12 mm wide; generally 1½ times as long as wide. The configuration is ovate with a crenate tip having an indention of approximately 1 mm. A variable lobe commonly is present on each side of the tip having a width of approximately 2 mm. The petal edges often curve inward approximately 2 mm and occasionally up to approximately 5 mm.

Color: Petal exterior Bright Rose (#58B) in tight bud becoming lighter Pink (#68C) by flowering and remaining essentially unchanged throughout anthesis. Petal interior is soft pink (#69A).

Sepals: Five in number and fold back at anthesis to form a star pattern. The configuration is generally rectangular with a sharp acute tip. The length commonly is approximately 3 to 4 mm and the base commonly is approximately 1 to 2 mm in width. The coloration is glossy green (#141D).

Stamens: The anthers are broadly elliptical, commonly measure approximately 1 to 1.5 mm, and are yellow (#12C) in coloration. Pollen is formed and is yellow (#12A) in coloration. Commonly approximately 17 to 19 filaments are present per flower and are arranged in an outward vase-shaped (stardust) pattern. The filaments typically are approximately 5 to 7 mm in length.

Pistil: Upright, with pilose-silky pubescence, white (#155D) in coloration, and commonly whorled around the base of the central filaments. The stigma commonly is approximately 2 mm in height and approximately 1 mm in width. The style is an elongated tubular structure having a length of approximately 1 mm and a width of approximately 0.5 mm. The style commonly is greyed-green (#193A) in coloration and is lightly covered with very short-pilose pubescence. The ovary is elongated subglobose to oblate-rounded in configuration, approximately 2 mm in length and approximately 1 mm in width, and green (#141C) in coloration.

LEAVES/FOLIAGE

The mature leaves have an attractive deep green, glossy surface and a firm, leathery texture. The arrangement is alternate. The upper (adaxial) surface is deep green and essentially glabrous except for slight short-pilose pubescence on the lower midrib and petiole and occasional short hairs on the veins. The lower (abaxial) surface is lighter matte green with short-pilose pubescence on the reddish midrib and veins and widely scattered on the surface. The margins are generally serrate to serrulate, often crenate, sometimes with the crenations imbricated. Both the leaf shape and size are somewhat variable. In general the leaves are basically ovate to lanceolate with an acute to short-acuminate apex and a rounded to slightly oblique base.

On the stronger shoots, the leaves are large, approximately 70–90 mm long by approximately 60–70 mm wide, and often have one or two lobes on each side. There are 3–6 prominent veins on each side of the midrib. Petioles are slender and mostly 12–20 mm long. The petioles bear stipules which range from large and prominently foliose (e.g. 8 mm long by 3 mm wide, serrate on a 3-lobed leaf approximately 70 mm long×approximately 60 mm wide) to mere 1 mm acute projections or simple auricles on the smaller, simpler leaves.

Leaves persist on the tree late into the fall, generally until hard freezes occur, usually mid-November near Dayton, Ohio.

Type: Simple, mostly entire, with serrate-crenate to serrulate-crenate margins.

Sape: Varies, mostly ovate to lanceolate with acute to acuminate tips and slightly oblique to obtuse-rounded bases; some leaves with one or two lobes on the side(s).

Size: Varies, length commonly in the approximately 60–75 mm range, width commonly approximately 35–55 mm, but many leaves may be considerably smaller.

Color: At maturity a glossy deep green (#135A) on the upper (adaxial) surface, paler with a matte surface underneath. Immature leaves Sap green (#135B).

FRUITS

The fruits are small, glossy, very firm, and subglobose to globose. The deciduous calyx leaves a small (about 1 mm) smooth grayish scar centered with a very small, shallow pit. They are borne in clusters of usually 4–5, ranging from 1 to approximately 7, on slender but sturdy purplish-red (#46D) pedicels approximately 20–30 mm long. The immature coloring varies with exposure to the sun but is generally an uneven greenish yellow. At peak maturity, the color is a brilliant bright red, retaining its glossiness and firmness into mid-December. The color darkens with exposure to freezing but the fruits remain firm with a degree of glossiness into February.

Shape: Subglobose to oblate-rounded, regular, slightly depressed at the juncture with the pedicel.

Size: Diameter varies, usually 10–12 mm. Often wider than deep, approximately 80 percent as deep as wide.

Color: At maturity brilliant bright red (#46A) darkening upon freezing (#183B). While immature, Sap green (#141C) with a slight glaucous bloom.

Skin: Very smooth, thin, glossy when mature; bearing a slight glaucous bloom while immature. Calyx scar smooth gray-brown, about 1 mm.

Pedicel: Slender but sturdy, slightly pubescent, purplish-red (#46D).

Season: Ripens September 15 to October 15 in Dayton, Ohio depending on the season. Fruit persists through late winter. Ornamentally effective throughout this season.

Seeds: Commonly approximately 3 to 5 seeds are formed per fruit that are ovate to lanceolate in configuration with an acute tip, and a Greyed-Orange (#172A) in coloration. Such seeds typically measure approximately 5 mm in length and approximately 2 mm in width.

TREE HABIT AND CHARACTER

The original specimen is now 15 years old, 15 feet high and 7 feet wide and is growing at a medium rate. The main trunk is very straight, erect, and sturdy. The branches are upright to pyramidal-spreading and sturdy. Overall, it is an excellently-shaped tree of relatively compact habit of growth. Trees propagated by budding having a height of approximately 180 cm, typically display a trunk diameter of approximately 31 mm when measured 15 cm above the ground.

Branching: Side branches diverge upwardly to slightly horizontally, making strong crotches. While typical branching angles are 50 to 60 degrees, branches of five years or older are generally 70 to 80 degrees.

Twigs: Young shoots are glossy olive green and glabrous. Current year stems are glossy rosewood (#187A) above on sun-exposed surfaces and darker gray brown (#176A) on shaded surfaces, and prominently lenticeled. The lenticels on one year old wood (#177A) are raised about 1 mm and are cream colored (#164D). Approximately 22 lenticels have been observed per 20 cm of a one year old shoot.

Buds: Reddish brown, generally ranging from 1 to 6 mm long, usually 2 to 4 mm. Commonly enclosed in 4 to 6 trident-apexed bud scales which are narrowly edged with short clear pilose-silky pubescence on the outer (adaxial) surface. Scales are also pubescent on the inner (abaxial) surface at the base, along the midribs, and on the tips. Terminal buds are narrowly conical tapering to an acute tip. Lateral buds are slightly compressed, broadly triangular in shape and appressed to the stem. Leaves in the bud and in the expanding buds bear non-persistent short, soft, clear hairs and small glandular hairs intermingled along the lower margins.

Bark: Similar to Prunus (cherry) bark of the same age in terms of color, texture and the presence of a slight sheen. The bark on two year old wood commonly is smooth in texture with a slight sheen and grey-brown (#199A) coloration, and bears lenticels that are rounded to ovate in configuration, smooth light tan to cream (#164D) in coloration and approximately 1 mm in size. The bark on five year old wood commonly has a thin smooth waxy texture with a slight sheen and grey-brown (#199A) coloration, and bears smooth lenticels that are light tan to cream (#164D) in coloration and commonly measure approximately 1×5 mm and occasionally up to 10 mm in size. The bark on ten year old wood of the original tree continues to be smooth, is greyed-green (#198A) in coloration, bears lenticels that are similar to those of the five year old wood, and bears some irregular patches of approximately 10 to 15 mm that are greyed-orange (#176A) in coloration. On the original tree from ground level up to a height of approximately 40 cm, the bark texture has changed to a cork with a thick, coarse, and rough texture and the coloration has remained greyed-green (#198A). On such tree some vertical bark cracking has appeared having openings that are approximately 5 to 10 mm in width and up to approximately 30 cm in length. Replacement bark within the exfoliating areas has a smooth texture and retains the greyed-green (#198A) coloration.

Pruning/Training requirements: Minimal, only in the liner stage to produce a commercially-desirable tree.

Hardiness: Survived 1996 winter temperatures of −30 degrees Celsius without damage and flowered profusely the following spring.

Productivity: Typically produces heavy flower and fruits crops annually. Flowers and fruits borne both on spurs on the older wood and in the axils of current-year growth. Clusters of five fruit are common.

We claim:

1. A new and distinctive variety of crabapple tree substantially as herein shown and described.

* * * * *